United States Patent [19]

Yoshida et al.

[11] Patent Number: 4,494,823
[45] Date of Patent: Jan. 22, 1985

[54] OPTICAL CONNECTOR SYSTEM

[75] Inventors: Kenichi Yoshida; Kimizo Ono; Tomio Iwamoto, all of Osaka, Japan

[73] Assignee: Sumitomo Electric Industries, Ltd., Osaka, Japan

[21] Appl. No.: 447,362

[22] Filed: Dec. 6, 1982

[30] Foreign Application Priority Data

Dec. 9, 1981 [JP] Japan .............................. 56-182156[U]
Mar. 8, 1982 [JP] Japan .................................. 57-37017
Sep. 17, 1982 [JP] Japan ............................ 57-140979[U]

[51] Int. Cl.³ ................................................. G02B 7/26
[52] U.S. Cl. ................................ 350/96.22; 350/96.18
[58] Field of Search ............... 350/96.18, 96.20, 96.21, 350/96.22

[56] References Cited

U.S. PATENT DOCUMENTS 3,455,625 7/1969 Brumley et al. .................. 350/96.22
4,279,465 7/1981 Vojvodich ........................ 350/96.20

FOREIGN PATENT DOCUMENTS 64619 11/1982 European Pat. Off. ......... 350/96.21

Primary Examiner—John Lee

Attorney, Agent, or Firm—Sughrue, Mion, Zinn, Macpeak, and Seas

[57] ABSTRACT

An optical connector system for combining light-receiving and light-transmitting optical fiber bundles has a male and female housing fitted to one end of light-transmitting and light-receiving bundles. The optical fiber bundles are held in the housings such that the end surface of a light receiving fiber bundle and that of a light-transmitting fiber bundle are simultaneously coupled to each other when the housings are joined. The female housing may contain a light-transmitting window and a light-receiving window such that when the male housing engages the female housing, the light-transmitting window faces the end surface of the light-transmitting fiber bundle and the light-receiving window faces the end surface of the light receiving bundle. The optical connector system may be used with a measuring apparatus having a main body with a light source having a light concentrating system, the female housing being connected to the main body such that with the male housing engaged with the female housing light from the light source is concentrated on the light-transmitting fiber bundle. A measuring portion of the measuring apparatus includes an image focusing system for focusing an image on the end-surface of the light-receiving fiber bundle on a slit.

13 Claims, 27 Drawing Figures

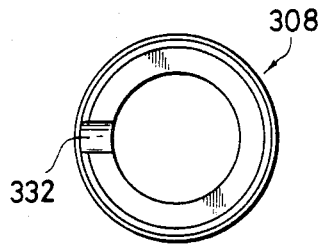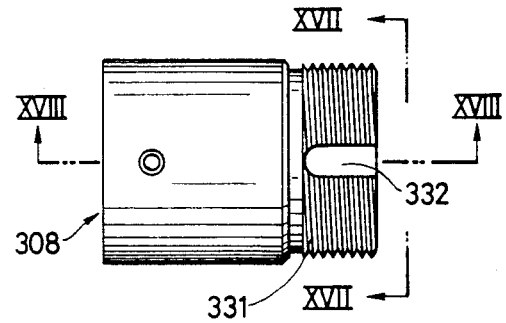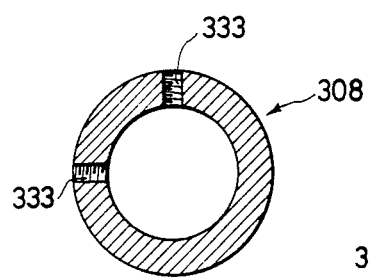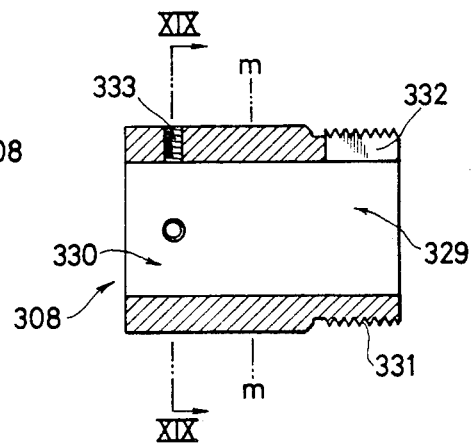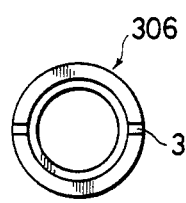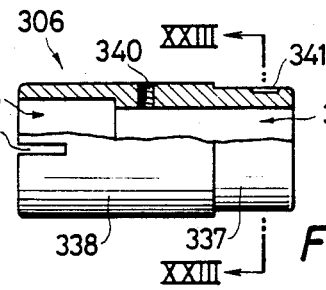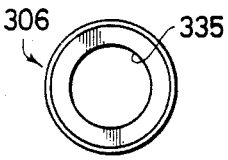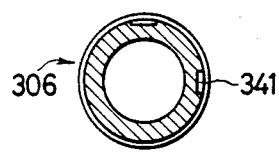

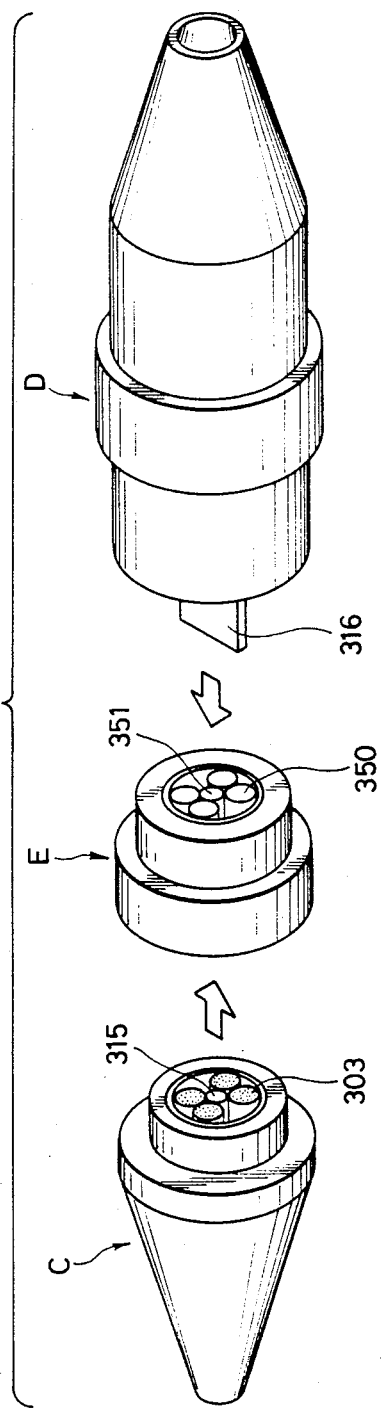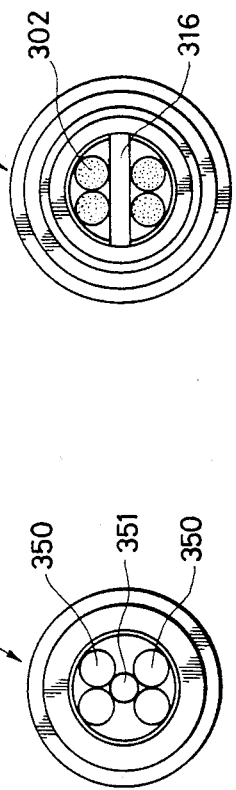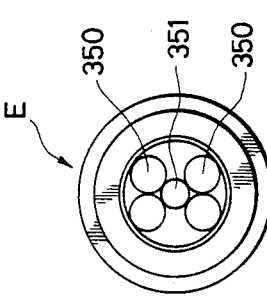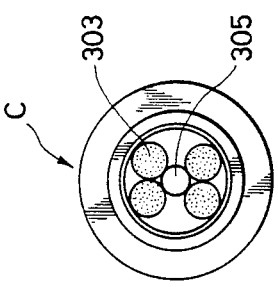

4,494,823

OPTICAL CONNECTOR SYSTEM

BACKGROUND OF THE INVENTION

This invention relates to an improved optical connector to connect two pairs of optical fibers, or optical fibers and light-receiving or light-transmitting elements to each other simultaneously.

Recently, optical fibers have increasingly found application and have been widely employed in medical instruments. For example, in a medical instrument for spectral analysis of living body tissue, light is transmitted and received through optical fiber bundles to measure the spectral characteristics of the tissues under study. Such an instrument for spectral analysis of living body tissue is shown in FIG. 1, wherein a light-transmitting fiber 2 for transmitting light therethrough from a light source 1 in section 6', a light-receiving fiber 3 for receiving light from the living body tissues, and a light-transmitting and receiving fiber 4 for a contact switch is provided to determine the timing for taking data. A probe 5 having a fiber bundle is used.

It is necessary for the probe 5 to be capable of being easily demounted from a main body 6 and sterilized, since it is introduced into a living body cavity. For this reason, conventionally, the probe 5 has been provided with a divergent point 5a. At this divergent point 5a, the probe 5 is separated into the light-transmitting fiber bundle 2, the light-receiving fiber bundle 3, and the contact switching fiber bundle 4, which are provided with the respective connectors 7, 8, 9 and 10 at top ends thereof. With these connectors, the probe 5 is connected to the instrument main body 6 and 6'.

Therefore, the structure of the probe 5 becomes complicated, and its mechanical strength is weakened. This creates inconveniences in the production and/or use thereof and increases production costs.

In operation, light is received through a slit 11 positioned on the back of the light-receiving connector 8 of the main body portion 6 to perform a spectral analysis. The above-described instrument, however, has the disadvantage that the exchange of the slit, which is performed to change its resolving power and light reception, for example, can be achieved only with difficulty.

Referring again to FIG. 1, a light source section 6' and a spectral analysis section 6 of the main body of the spectral analysis system are separated from each other by a partition 6" so that transmitted and received light does not interfere with each other. The portions 6 and 6' are provided with female housings 7 and 8, respectively, of an optical connector assembly. When the male housings 12 and 12' are plugged in the female housings 7 and 8, respectively, light from a light source in the light source section 6' is concentrated on the end of the light-transmitting fiber by means of condensing lens 14 (having a fairly large diameter since it is necessary to concentrate a large quantity of light of about from 1 to 10 mw at the end of the light-transmitting fiber), and is sent through the light-transmitting fiber bundle 2 to a measuring point 15 where the tissue is illuminated. The light from the tissue is received through the light-receiving fiber bundle 3 on a slit 11 in the spectral analysis section 6 and, thereafter, analysis is performed by means of the spectral analysis system.

Another defect of the above-described prior art apparatus resides in that the fiber bundle 5 is separated into the light-transmitting fiber bundle 2 and the light-receiving fiber bundle 3 at the divergent point 5a. Specifically, this often causes problems such as fiber-cutting. Furthermore, since the female housing 7 for the light-transmitting fiber and the female housing 8 for the light-receiving fiber bundle should be provided separately in the main body of the analytical apparatus, the arrangement of the light source section 6' and the spectral analysis section 6 which should be placed as closely as possible is limited, preventing miniaturization of the apparatus.

SUMMARY OF THE INVENTION

The present invention is intended to overcome the above-described defects of the prior art techniques.

It is an object of the invention to provide an optical connector which permits easy connection of optical fibers, and in which the slit can be easily exchanged.

It is another object of this invention to provide a connector for optical fibers at an intermediate point that insures proper alignment.

The present invention, therefore, relates to an optical connector comprising a pair of housings wherein one of the housings contains a plurality of optical fibers, or light-receiving and light-transmitting elements in the fixed condition, and the other housing contains a plurality of optical fibers in the fixed condition. The optical fibers being provided to face the optical fibers, or light-receiving and light-transmitting elements contained in the opposite housing, so that at least two pairs of optical fibers, or optical fibers and light-receiving or light-transmitting elements can be connected to each other simultaneously.

In accordance with another aspect of the invention, the male housing for the light-transmitting fiber bundle and the male housing for the light-receiving fiber bundle are combined together into a single male housing, and the slit is provided not directly on a light-receiving window, but at a position spaced apart by means of an optical system where the image is formed. Hence, light-shielding between the light source section and the spectral analytical section can be achieved with ease.

In accordance with yet another embodiment of this invention, an intermediate connector for fiber bundles, comprises a first connector portion holding therein a fiber bundle or bundles and a second connector portion holding therein the same number of fiber bundles. The first and second connector portions can be connected to or separated from each other, and are arranged so that the corresponding fiber bundles contained therein face each other. The fiber bundle contains a light-transmitting fiber and a light-receiving fiber and a slit plate is provided at a joint to separate them from each other. A lens may be placed between the faces of the corresponding fiber bundles.

The preferred embodiments of the invention will be explained in detail by reference to the accompanying drawings.

BRIEF DESCRIPTION OF THE DRAWINGS

FIG. 16 is a plan view of a plug;

FIG. 17 is a view taken in the direction of the arrow along the line XVII—XVII of FIG. 16;

FIG. 18 is a cross-sectional view taken along the line XVIII—XVIII of FIG. 16;

FIG. 19 is a cross-sectional view taken along the line XIX—XIX of FIG. 18;

FIG. 20 is a front view of a plug core with parts partially broken away;

FIG. 21 is a left side view of the plug core;

FIG. 22 is a right side view of the plug core;

FIG. 23 is a cross-sectional view taken along the line XXIII—XXIII of FIG. 20;

FIG. 24 is a perspective view of an intermediate connector for fiber bundles, utilizing a lens system, in the dismantled condition;

FIG. 25 is a side view of a first connector portion;

FIG. 26 is a side view of a lens tube portion; and

FIG. 27 is a side view of a second connector portion.

DESCRIPTION OF THE PREFERRED EMBODIMENTS

Figure 1:
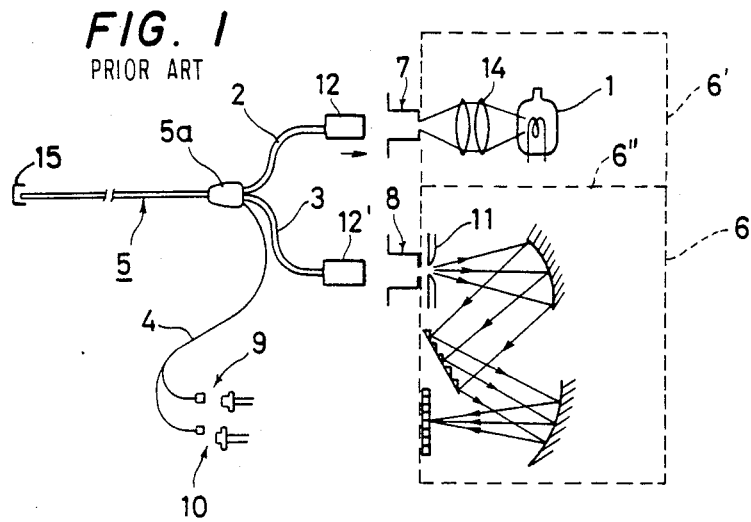
FIG. 1 is a schematic view of a conventional optical connector as used in combination with a living body tissue spectral analytical apparatus.
Figure 2:
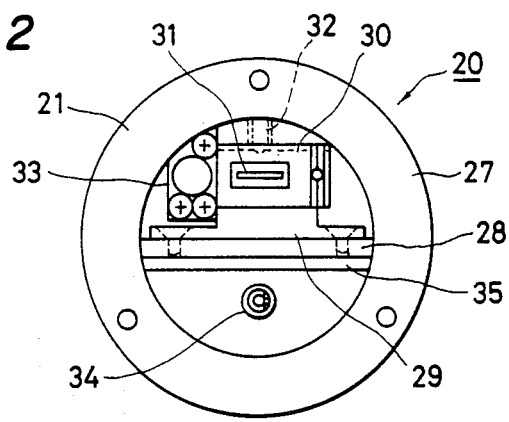
FIGS. 2 and 3 are a front view and a longitudinal sectional view, respectively, of a first embodiment of the optical connector of the invention.
Figure 3:
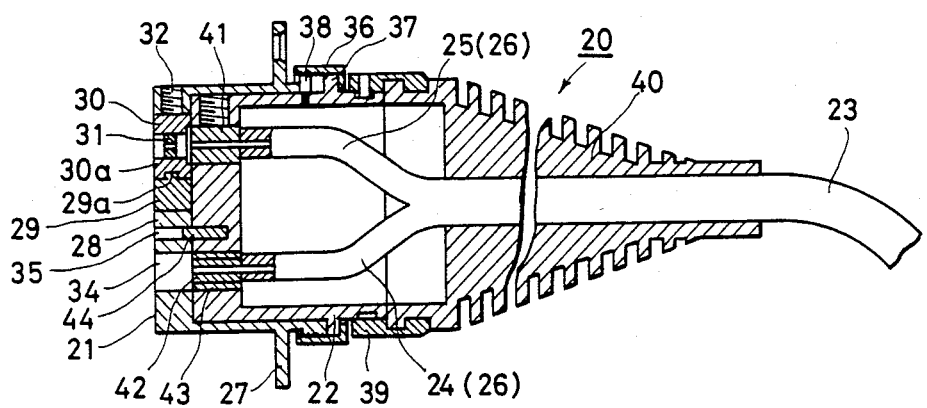

FIGS. 2 and 3 are a front view and a longitudinal sectional view, respectively, of a first embodiment of the optical connector of this invention. An optical connector 20 comprises a female housing 21 and a male housing 22, the female housing 21 being fitted to the fixed side including a spectral analytical apparatus and the like of FIG. 1. The male housing 22 is plugged in and connected to the female housing 21. A light-transmitting fiber 24 and a light-receiving fiber 25 for spectral analysis, and a light-transmitting and receiving fiber 26 for a contact switch, all contained in the bundle fiber 23, are connected to the housing 22.

The female housing 21 is nearly cylindrical. At the periphery of the top portion of the female housing 21, a male screw is formed for connecting the female housing 21 to the male housing 22. At the periphery of the intermediate portion a fixing flange 27 is provided. Inside the female housing 21, a one-piece beam 28 is provided horizontally at the central portion thereof and a slit substrate 29 is bolted onto the top surface of the beam 28 (FIG. 2). On the top surface of the slit substrate 29, a convex portion 29a is formed to be plugged in a concave portion 30a of a slit-fixing base 30. Thus, the slit-fixing base 30 can be mounted or demounted from the side of the female housing 21. The slit-fixing base 30 is supported by the top end of a ball plunger 32 which is positioned at the central position above the beam 28. The slit 31 is fixed on the slit-fixing base 30 and is disposed downward from the upper portion of the female housing 21.

A sensor-fixing base 33, on which a light-receiving photodiode of a contact sensor to be mounted, is fitted to the female housing 21 in such a manner that it is positioned at the side of the slit 31. The photodiode is mounted on the sensor-fixing base 33. At the central position below the beam 28, a hole 34 is formed and is used to transmit light from a light source to the light-transmitting fibers 24 and 26 fitted in the male housing. In the beam 28, a long hole 35 is bored through which a shield plate is to be fitted. The shield plate is provided to prevent the light from a light source from directly entering the slit 31 or the sensor.

The male housing 22 is nearly cylindrical. The periphery of the top end portion is configured so that it can be plugged in the female housing 21. On the periphery of the central portion, a flange 37 is formed coming into engagement with a nut 36 which is used to connect the male housing 22 to the female housing 21. That is, the male housing 22 is connected to the female housing 21 by screwing the nut 36 on the male screw of the female housing 21. To achieve this positioning, a groove is formed in the female housing 21 in the axial direction thereof. By fitting the bolt 38 along the groove, it being screwed in the male housing 22, accurate positioning can be achieved.

The male housing 22 is provided at the base end portion thereof with a boot 40 which is fixed to the housing 22 by a linking ring 39. Through the boot 40, the fiber bundle 23 is introduced into the male housing 22. The light-receiving fiber 25 portion of fiber bundle 23 is bolted through a holder 41 at a position facing the slit 31 of the female housing 21. The light-transmitting fiber 24 is fitted through a notched sleeve 42 at a position facing the hole 34. At the periphery of the notched sleeve 42, through a sleeve 43, the light-transmitting fiber 26 for a contact sensor is fitted. In this way, the double structure is formed, and a light source is supplied. The light-receiving fiber 26 for the contact sensor is fitted at a position facing the light-receiving photodiode of the female housing 21. A shield plate 44 prevents interference between transmitted light and received light and projects from the male housing 22. The shield plate 44 can be plugged in the long hole 35 of the female housing 21.

By employing the construction as described above in which the female housing 21 is fixed in the main body of the spectral analytical apparatus and the male housing 22 is plugged in the female housing 21 and connected thereto by means of the nut 36, a plurality of optical fibers, or light-receiving and light-transmitting elements can be connected to each other at the same time using only one optical connector. Further, the shield plate 44 prevents transmitted light from leaking to the light-received side. Moreover, it is not necessary to provide a divergent point for the fiber bundle at the outside of the instrument, where the fiber bundle is allowed to diverge. This increases mechanical strength and reliability and further lowers production costs.

Figure 4:
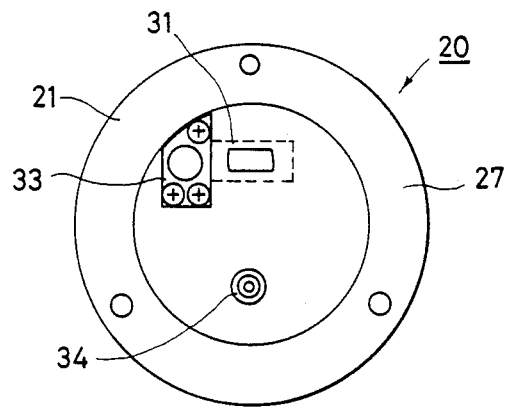
FIGS. 4 and 5 are a front view and a longitudinal sectional view, respectively, of a second embodiment of the invention.
Figure 5:
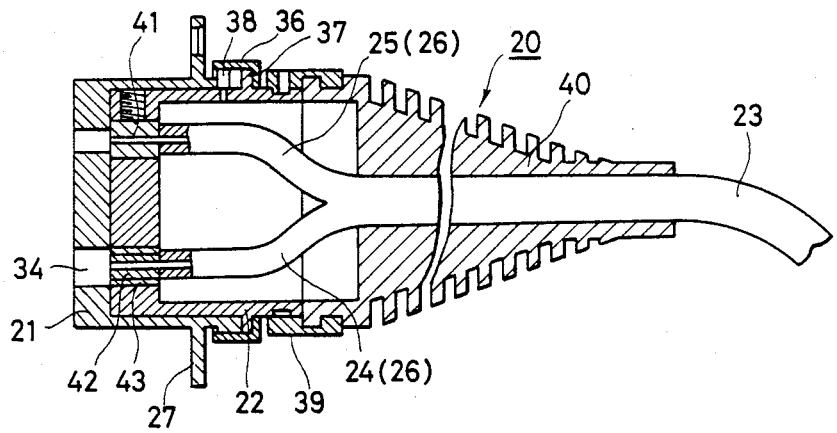

FIGS. 4 and 5 illustrate a second embodiment of the invention, which is of the same type as in the above-described first embodiment except that the slit and the shield plate are not installed in the inside of the connector. That is, an optical connector 20 comprises a female housing 21 and a male housing 22. A light-transmitting fiber 24 and a light-receiving fiber 25 for a spectral analysis, and a light-transmitting and light-receiving fiber 26 for a contact switch are all contained in a fiber bundle 23 and are connected to the housing 22. The female housing 21 is fitted to the main body of a spectral analytical apparatus. By fitting the male housing 22 into the female housing 21 and connecting them by means of a nut 36, a plurality of optical fibers, or light-receiving and light-transmitting elements can be connected simultaneously using one optical connector. The structure is simplified, vis-a-vis the first embodiment, leading to easy use and further reduced production costs.

Figures 6, 7:
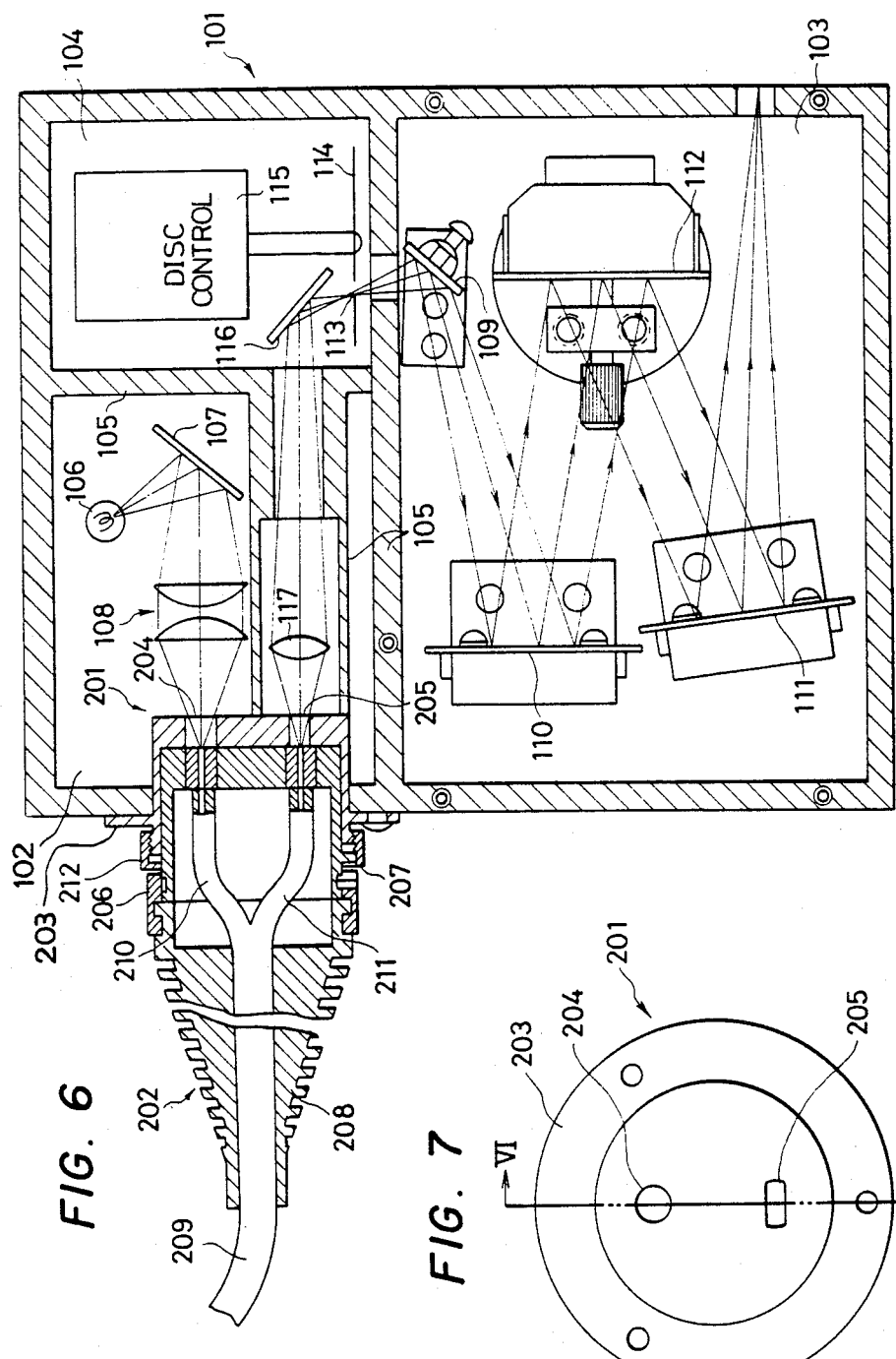
FIG. 6 is a cross-sectional view of a living body spectral analysis apparatus in accordance with a third embodiment of the invention.
FIG. 7 is a top view of the female housing in the embodiment of FIG. 6.

FIGS. 6 and 7 illustrate how the connectors of the first two embodiments can be utilized in conjunction with the analysis section 6 and the light-transmitting section 6' by coupling into only one section. Hence, in this embodiment the connectors 7 and 8 in FIG. 1 are combined into only one portion of the system.

Referring now to FIG. 6, a spectral analysis system, comprising a main body 101, a light source section 102, a spectral analytical section 103, a slit section 104, a light-shielding wall 105 optically separating the light source section 102, the spectral analytical section 103, and the slit section 104 from each other is shown. A female housing 201 and a male housing 202 couple the analysis and light-transmission portions to the probe.

In the light source section 102, a light source 106, a reflector 107, and a set of condensing lenses 108 are disposed. In the spectral analytical section 103, a plurality of reflectors 109, 110 and 111, a diffraction grating 112, and their controlling devices are disposed. In the slit section 104, a disc 114 is disposed having a plurality of slits 113 at the same radial location. A disc-controlling device 115 for rotating the disc 114 to the desired position and stopping it at the desired position, together with a reflector 116, and a lens 117 are placed.

The female housing 201 is fitted to an opening provided in the wall of the main body 101 of the spectral analysis apparatus by means of a plurality of screws through screw holes provided in a flange portion 203, and is provided with an opening 204 for transmitting light and an opening 205 for receiving light at the bottom thereof. FIG. 7 is a plan view of the female housing 201. The cross-section of housing 201 taken along the line VI—VI is shown in FIG. 6.

The male housing 202 similar to the embodiment of FIG. 5 comprises a male housing main body 207 linked by a connecting link 206 together with a flexible boot 208 made of rubber or a material similar to rubber. A fiber bundle 209 is introduced into the main body 207 through the boot 208. The fiber bundle 209 diverges into a light-transmitting fiber bundle 210 and a light-receiving fiber bundle 211 in the male housing main body 207. The respective ends of the light-transmitting and light-receiving fiber bundles 210 and 211 are fixed at the positions corresponding to the light-transmitting and light-receiving openings 204 and 205 in the female housing 201. Reference numeral 212 indicates a nut which is used to fix the male and female housings 202 and 201 after the engagement thereof.

In this embodiment, the female housing is provided in the measuring apparatus main body side and the male housing in the fiber bundle 209 side, the same effect can be obtained even when the male housing is provided in the main body side and the female housing in the fiber bundle side.

In accordance with this embodiment, the fiber bundle is designed so that it diverges in the housing, and the structure is produced in which the divergent point is inside the housing unlike the conventional device of FIG. 1 where trouble occurs at the divergent zone. Further, the structure is designed so that the slit 113 is present in the inner part of the apparatus, and the contact between the slit 113 and the light-receiving fiber portion is attained by an optical system containing the reflectors and the like. Hence, even when the light-transmitting optical axis and the light-receiving optical axis are provided so that they are relatively close to each other, the light-shielding between them can be easily achieved. This permits significant miniaturization of the apparatus.

As indicated herein a fiber bundle for medical purposes is used to examine organs such as the stomach, liver, other organs, tissues, and so forth. Depending on the region to be examined, it is necessary to use a sensor portion having the suitable shape, dimension, and structure. In conventional medical instruments utilizing such fiber bundles, since the sensor portion and the entire fiber bundle are produced in one piece, it has been necessary to exchange the entire fiber bundle depending on the subject of examination. It is, however, convenient to exchange only the top portions of the fiber bundle, including the sensor portion.

The present invention is intended to meet the above-described requirements. Thus, it also relates to an intermediate connector for fiber bundles, which is provided demountably at an intermediate point of the fiber bundle, and in which the fibers are arranged so that the ends of the corresponding ones face each other. Such an intermediate connector is shown in FIG. 1 as element 5a.

Figures 8, 9, 10:
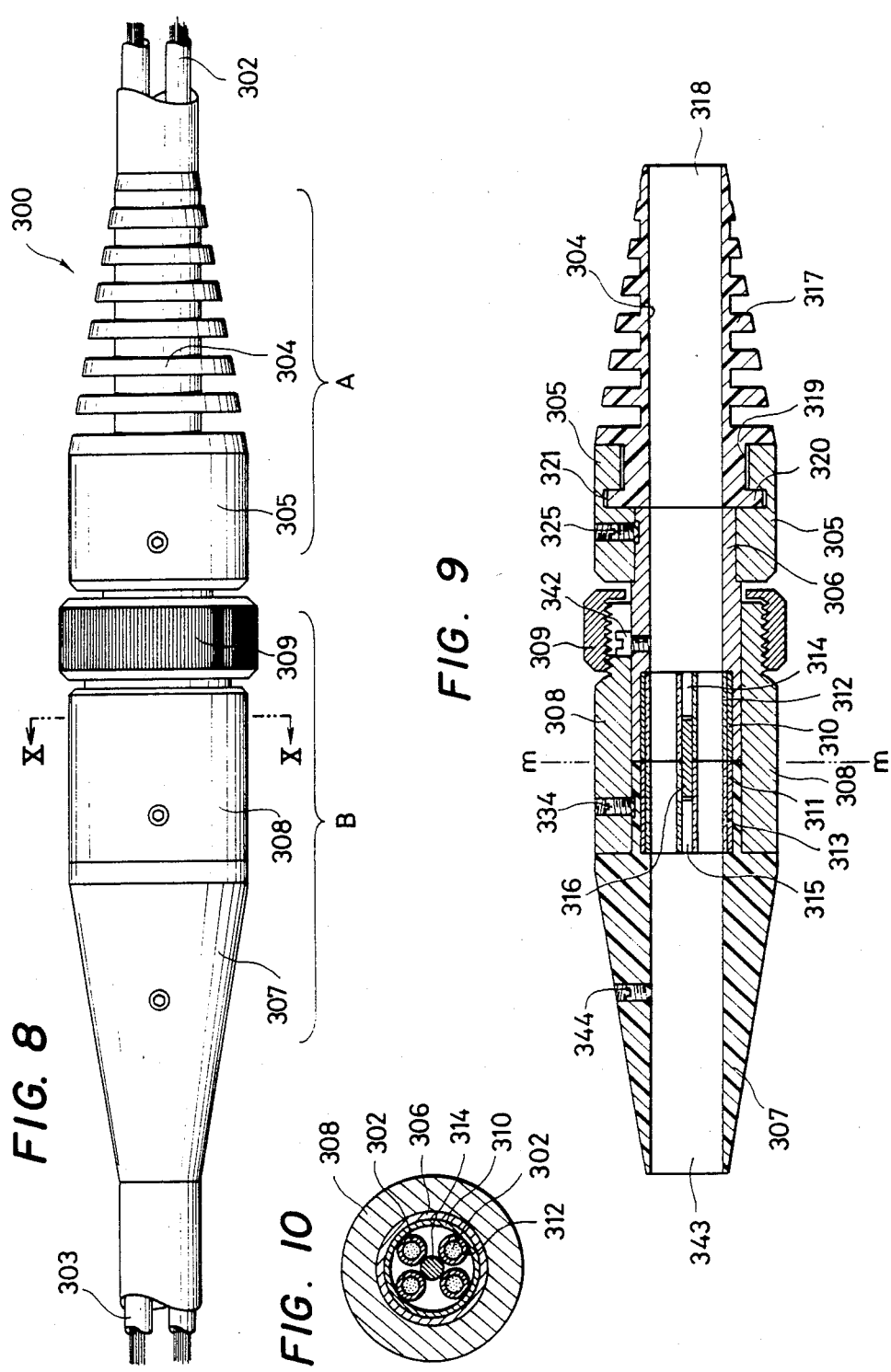
FIG. 8 is a plan view of an intermediate connector for fiber bundles according to the present invention.
FIG. 9 is a longitudinal sectional view of the intermediate connector for fiber bundles.
FIG. 10 is a sectional view taken along the line X—X of FIG. 8.

FIG. 8 is a plan view of an intermediate connector for fiber bundles in accordance with this invention, and FIG. 9 is a longitudinal sectional view of the intermediate connector of FIG. 8. FIG. 10 is a cross section view along section line X—X of FIG. 8. Referring to these Figures, an intermediate connector 300 for fiber bundles connects a fiber bundle 302 and a fiber bundle 303 to each other at an intermediate point, or separates them from each other.

The intermediate connector 301 comprises a bushing 304, an adaptor 305, a plug core 306, a conical member 307, a plug 308, a clamping nut 309, external sleeves 310 and 311, central sleeves 312 and 313, spacers 314 and 315, and a slit plate 316.

The bushing 304 is made of a flexible material, e.g., plastics and rubber, is cylindrical in shape, and is provided with a plurality of protective rings 317 at the periphery thereof, the protective rings being tapered. A bushing 304 is bored in its longitudinal direction with a hole 318 through which a fiber core is passed. In this case, four fiber cores are inserted into the bushing 304, and in order that the fiber cores are not excessively bent, the protective rings 317 are formed.

The front portion of the bushing 304 is designed so that a concave portion 319 having a reduced diameter is followed by a portion 320 having an extended diameter, so that the bushing 304 can be connected by plugging in the adaptor 305.

Figures 11, 12, 13:
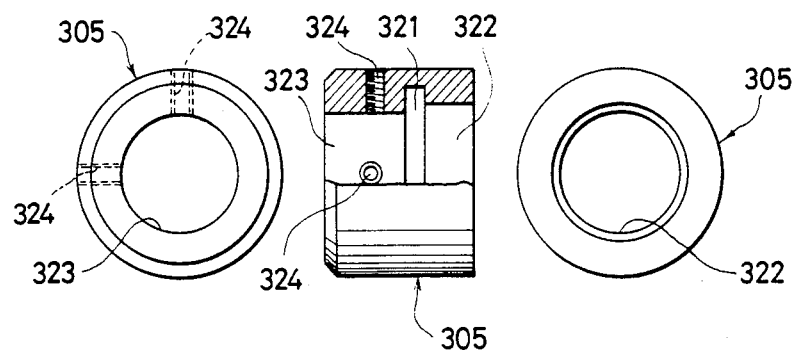
FIG. 11 is a partially cut away front view of an adaptor.
FIG. 12 is a left side view of the adaptor.
FIG. 13 is a right side view of the adaptor.

FIG. 11 is a partially cut away front view of the adaptor 305. FIG. 12 is a left side view of the adaptor 305, and FIG. 13 is a right side view of the adaptor 305.

The adaptor 305 is short and cylindrical in shape, and a concave line 321 is provided in the adaptor 305 on the inner surface at an intermediate point thereof. This concave line 321 is provided so that the diameter-extended portion 320 of the bushing 304 can be inserted to secure it therein.

The bushing 304 following the concave line 321 of the adaptor 305 has a slightly larger inner diameter. The portion preceding the concave line 321 is a plug core-inserting hole 323 which has a reduced inner diameter, into which the plug core 306 is to be inserted. In the adaptor 305, two female screw holes 324 are bored at both sides thereof. Through the hole 324 a hexagonal head bolt 325 (FIG. 9) to secure the plug core 306.

Figures 14, 15:
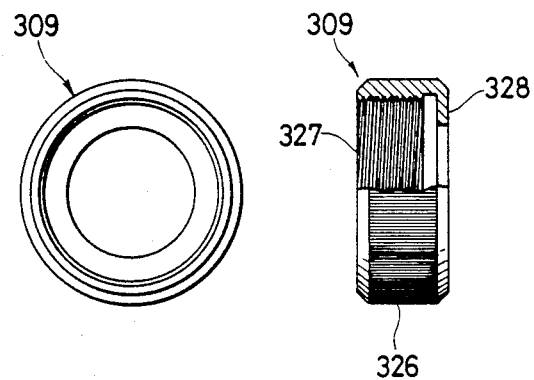
FIG. 14 is a partially cut away front view of a clamping nut.
FIG. 15 is a left side view of the clamping nut.

FIG. 14 is a partially cut away front view of the clamping nut 309, and FIG. 15 is a left side view of the clamping nut 309. The clamping nut 309 is provided with a knurled area 326 on the periphery thereof so that it can be easily turned manually. A female screw line 327 is engraved in the inner surface of the clamping nut 309 and one end of the clamping nut 309 terminates in a flange 328. By bringing the clamping nut 309 into engagement with the plug 308 and reducing its diameter in the inward direction, the plug 309 is fastened to the plug core 306.

FIG. 16 is a plan view of the plug 308, FIG. 17 is a view taken in the direction of the arrow along the line XVII—XVII of FIG. 16. FIG. 18 is a cross-sectional view taken along the line XVIII—XVIII of FIG. 16 and FIG. 19 is a cross-sectional view taken along the line XIX—XIX of FIG. 18. As shown in these Figures, the plug 308 is cylindrical, bored in its axial direction with a hole having a defined inner diameter. At the right hand side from a central line m, a plug core-inserting hole 329 is provided, into which the plug core is to be inserted. At the left hand side from the central line m, a conical cylindrical member-inserting hole 330 is disposed in which the conical cylindrical member 307 is plugged and secured.

A male screw line 331 is engraved in the periphery of the plug core-inserting hole 329. The clamping nut 309 comes into engagement with the male screw line 331. The portion bearing the male screw line 331 is notched to form a turning-stopping groove 332 which is opened at one end. A female screw hole 333 (FIGS. 18, 20) is bored in the plug from the side thereof, reaching the conical cylindrical member-inserting hole 330. In the female screw hole 333, a hexagonal head bolt 334 is screwed (FIG. 9) to prevent the conical cylindrical member 307 from coming out therefrom.

FIG. 20 is a partially cut away front view of the plug core 306. FIG. 21 is a left side view and FIG. 22 is a right side view of the same element. FIG. 23 is a cross-sectional view taken along the line XXIII—XXIII of FIG. 20. A shown in these Figures, the plug core 306 is cylindrical, but its inside is composed of two chambers, one having a large inner diameter and the other a small inner diameter. The chamber having a small inner diameter is a fiber core-inserting hole 335, and the chamber having a large inner diameter, an external sleeve-inserting hole 336. The outer surface of the plug core 306 is also divided into two portions, having a large outer diameter and a small outer diameter. One portion having a small outer diameter is an adaptor-inserting part 337 which is to be inserted in the plug 305 and fixed firmly therein, and the other portion having a large outer diameter is a plug-inserting part 338. The plug-inserting part 338 can be inserted in and removed from the plug 308. Two grooves 339 are formed in the front end of the plug-inserting part 338 such that they are in an opposite relation respective to the center. A slit plate 316 is inserted in the groove 339 to prevent the interference between light-transmitting and light-receiving fibers.

A female screw hole 340 is bored in the plug core 306 at the middle thereof. Two concave portions 341 are provided in the back portion of the plug core 306. A turn-stopping screw 342 (FIG. 9) is driven in the female screw hole 340. When the connector is assembled, the turn-stopping screw 342 is inserted in the turn-stopping groove 332 of the plug 308. The relative position in the direction of angle between the plug 308 and the plug core 306 is therefore determined. The bushing 304, the adaptor 305, and the plug core 306 are produced in one piece, forming a first connector portion A as shown in FIG. 8. The conical cylindrical member 307, the plug 308, and the clamping nut 309 constitute a second connector portion B.

The four fiber bundles 302 are introduced through the fiber core-passing hole 318 of the bushing 304, and then, through the fiber core-passing hole 335 of the plug core 306 into the intermediate sleeve 312 where their top ends are fixed. The other four fiber bundles 303 are introduced through the fiber core-passing hole 343 of the conical cylindrical member 307 into the intermediate sleeve 313 where their top ends are fixed. The outer sleeves 310 and 311 are provided to enclose the intermediate sleeves 312 and 313. The fibers in the fiber bundle 302 or 303 face exactly the respective ones in the opposite fiber bundle with the central line m as a plane therebetween. Spacers 314 and 315 are cylindrical members which are fixed on the circular inner surfaces to firmly hold in position the fiber bundles having a circular cross section.

The slit plate 316 is used to prevent the interference between light-transmitting and light-receiving fibers in the fiber bundles 302 and 303 at the plane as described above. A hexagonal head bolt 344 is used to prevent the fiber core bundle from coming out of the conical cylindrical member 307.

When the clamping nut 309 is tightened, the plug 308 is bent toward the inner side because it is provided with the turn-stopping groove 332. For this reason, the inner surface of the plug 308 presses uniformly against the outer surface of the plug core 306. This pressure produces a significant frictional force between the plug 308 and the plug core 306. As a result, the plug 308 and the plug core 306 are firmly bonded together and cannot easily be separated. In this way, the first and second connector portions A and B are linked together.

Conversely, when the clamping nut 309 is loosened, the plug core 306 can be taken out of the plug 308. Thus, the first and second connector portions A and B can be separated.

The above-described embodiment is an intermediate connector for fiber bundles, in which the fiber bundles are disposed to directly face each other.

The present invention includes another embodiment of the intermediate connector in which a lens is placed between the fiber bundles. In this embodiment, since light is concentrated by the lens system, the bond efficiency between the fiber bundles is increased. Furthermore, as well as fiber bundles having the same diameter, those having different diameters can also be linked together efficiently. FIG. 24 is a perspective view of an intermediate connector for fiber bundles, in which a lens system is used.

The connector shown in FIG. 24 comprises three components, a first connector portion C, a second connector portion D, and a lens tube portion E. In the lens tube portion E, a rod lens 350 is positioned in such a manner that the rod lens 350 faces the fiber bundles 302 and 303. In the middle of the rod lens, a spacer 351 is provided.

FIGS. 25, 26 and 27 are side views of the first connector portion C, the lens tube portion E, and the second connector portion D, respectively. The rod lens 350 has two functions. One of the functions is an improvement in bonding efficiency. For example, when a ½ pitch refractive index distribution type lens is used, since the image on the end surface of the opposite fiber bundle is focused at a rate of 1:1, the bonding efficiency can be increased.

The other function of the lens is that it can link fiber bundles having different diameters to each other. For example, when a ¼ pitch refractive index distribution type lens is used, the central line of the lens deviates from the center between fiber end surfaces. Further, the fiber end surface is placed at a point where the image is focused, the image on the fiber end surface can be enlarged or reduced. Therefore, fibers having different diameters can be linked together.

With this aspect of the invention, the intermediate connector facilitates connection and separation of fiber bundles at the intermediate position thereof. This allows for separation and sterilization of the bundle and the sensor without handling the complete system.

It is apparent that the invention is capable of other modifications not specifically delineated herein but within the scope thereof.

We claim:

1. An optical connector comprising: a pair of housings; one of the housings containing a plurality of light-receiving and light-transmitting elements in a fixed condition, the other housing containing a plurality of optical fiber bundles in a fixed condition, said optical fiber bundles in said other housing being provided to face the light-receiving and light-transmitting elements in said one housing, wherein at least one pair of optical fiber bundles can be connected to said light-receiving and light-transmitting elements simultaneously when said housings are in an opposed relationship; and wherein one of said housings comprises a female member receiving therein the other housing defining a male member, said female member comprising an internal horizontal brace with a slit mounted thereon, said male member having an internal holder for securing one of said optical fiber bundles facing said slit, said female member further comprising a hollow zone, said male member further comprising a notched sleeve receiving another of said fiber bundles in said male member to confront said hollow zone in said female member, and means to secure said female member to said male member.

2. The connector of claim 1, wherein one of said fiber bundles is a light-receiving bundle confronting said slit and another of said bundles is a light-transmitting bundle confronting said hollow zone, and a shield plate positioned between said light-receiving bundle and said light-transmitting bundle and extending into said female member.

3. The connector of claim 1, wherein said female member further includes a sensor fixing base positioned to one side of said slit, and a contact sensor including a photodiode mounted on said sensor fixing base.

4. An optical connector comprising: a pair of housings; one of the housings containing a plurality of light-receiving and light-transmitting elements in a fixed condition, the other housing containing a plurality of optical fiber bundles in a fixed condition, said optical fiber bundles in said other housing being provided to face the light-receiving and light-transmitting elements in said one housing, wherein at least one pair of optical fiber bundles can be connected to said light-receiving and light-transmitting elements simultaneously when said housings are in an opposed relationship; and wherein one of said housings comprises a female member receiving therein the other housing defining a male member, said male member comprising a first holder for one of said fiber bundles and a second holder for another of said fiber bundles for respectively fixing the position of said fiber bundles in said male member, said female member comprising a pair of through-holes confronting said fiber bundles and, means for locking said male and said female members together.

5. The connector of claim 4, wherein said light-receiving and light-transmitting elements comprise a second pair of fiber bundles and wherein said connector is an intermediate connector between two pairs of fiber bundles.

6. The connector of claim 5, wherein said housings comprise a first connector portion holding therein at least one fiber bundle and a second connector portion holding therein the same number of fiber bundles held in said first connector portion, wherein the first and second connector portions can be connected to or separated from each other, and are arranged so that the corresponding fiber bundles contained therein face each other.

7. The connector of claim 6, wherein each fiber bundle contains a light-transmitting fiber and a light-receiving fiber, and a slit plate provided at a joint to separate said light-receiving fiber and said light-transmitting fiber from each other.

8. The connector of claim 6 further comprising a lens placed between the faces of the corresponding fiber bundles.

9. An optical connector comprising: a pair of housings; one of the housings containing a plurality of light-receiving and light-transmitting elements in a fixed condition, the other housing containing a plurality of optical fiber bundles in a fixed condition, said optical fiber bundles in said other housing being provided to face the light-receiving and light-transmitting elements in said one housing, wherein at least one pair of optical fiber bundles can be connected to said light-receiving and light-transmitting elements simultaneously when said housings are in an opposed relationship; wherein one of the fiber bundles comprises a light-transmitting bundle and another of said fiber bundles comprises a light-receiving bundle; and wherein one of said housings comprises a female member, and the other housing a male member, means to lock the members together, said female member having a light-transmitting window and a light-receiving window, said light-transmitting and light-receiving windows configured so that, when the male member comes into engagement, the light-transmitting window faces the end surface of the light-transmitting fiber bundle, and the light-receiving window faces the end surface of the light-receiving fiber bundle.

10. The connector of claim 9 further comprising a main body having a light source portion including a light-concentrating optical system which, when the female housing is fitted, and the male housing comes into engagement with the female housing, concentrates light on the end surface of the light-transmitting fiber bundle; and a measuring portion including image-focusing optical means for focusing the image on the end surface of the light-receiving fiber bundle on a slit.

11. The connector of claim 10 further comprising a light-shielding member provided between the light source portion and the measuring portion.

12. The connector of claim 10, wherein said main body comprises a light source section, a spectral analysis section and a slit section, said light-concentrating optical system disposed in said light source section, said slit being disposed on a disc, means disposed in said slit section for rotating said disc and reflector means in said spectral analysis section receiving light passing through said slit.

13. The connector of claim 12, wherein said female member is fixed to said main body, and said image-focusing means comprises a lens positioned in said main body and a reflector for directing said image on the end surface of the light-receiving fiber bundle focused by said lens onto said slit.

* * * * *